United States Patent
Brown (10) Patent No.: US 7,866,211 B2
(45) Date of Patent: Jan. 11, 2011

(54) FOULING AND CORROSION DETECTOR FOR PROCESS CONTROL INDUSTRIES

(75) Inventor: Gregory C. Brown, Chanhassen, MN (US)

(73) Assignee: Rosemount Inc., Eden Prairie, MN (US)

( * ) Notice: Subject to any disclaimer, the term of this patent is extended or adjusted under 35 U.S.C. 154(b) by 0 days.

(21) Appl. No.: 10/924,277

(22) Filed: Aug. 23, 2004

(65) Prior Publication Data

US 2006/0037399 A1    Feb. 23, 2006

Related U.S. Application Data

(63) Continuation-in-part of application No. 10/893,144, filed on Jul. 16, 2004, now Pat. No. 7,290,450.

(51) Int. Cl.
*G01N 29/036* (2006.01)

(52) U.S. Cl. .............. 73/579; 73/54.25; 73/86; 73/580

(58) Field of Classification Search ............. 73/579, 73/580, 599, 600, 602, 861.18, 862.59, 54.41, 73/53.05, 64.42, 24.06, 861.356, 861.357, 73/86; 340/606
See application file for complete search history.

(56) References Cited

U.S. PATENT DOCUMENTS

| | | | | |
|---|---|---|---|---|
| 3,060,377 A * | 10/1962 | Schmidt | ............. | 324/220 |
| 3,204,455 A * | 9/1965 | Kallmann | ............. | 73/861.26 |
| 3,625,057 A * | 12/1971 | Yoshiyama et al. | ...... | 73/861.27 |
| 4,605,065 A | 8/1986 | Abercrombie | ............. | 166/250 |
| 4,696,191 A * | 9/1987 | Claytor et al. | ............. | 73/600 |
| 4,783,987 A * | 11/1988 | Hager et al. | ............. | 73/32 A |
| 4,924,710 A | 5/1990 | Inada et al. | ............. | 73/861.23 |
| 5,003,295 A | 3/1991 | Kleven | ............. | 340/581 |
| 5,031,456 A * | 7/1991 | Askwith et al. | ............. | 73/587 |
| 5,208,162 A | 5/1993 | Osborne et al. | ............. | 436/6 |
| 5,372,046 A * | 12/1994 | Kleven et al. | ............. | 73/861.22 |
| 5,429,001 A | 7/1995 | Kleven | ............. | 73/861.22 |
| 5,509,311 A | 4/1996 | Lew | ............. | 73/661 |
| 5,519,330 A * | 5/1996 | Yamauchi et al. | ............. | 324/700 |

(Continued)

FOREIGN PATENT DOCUMENTS

CN    1022133 C    9/1993

(Continued)

OTHER PUBLICATIONS

Decca, R.S.; Drew, H.D.; Empson, K.L. Mechanical Oscillator Tip-To-Sample Separation Control for Near-Field Optical Microscopy American Institute of Physics, 1997, pp. 1291-1295.

(Continued)

*Primary Examiner*—J M Saint Surin
(74) *Attorney, Agent, or Firm*—Westman, Champlin & Kelly, P.A.

(57) ABSTRACT

A method for inferring possible or impending corrosion or fouling of process elements from fluid flowing in a pipe of an industrial process is described. A frequency response of a body is measured. The measured frequency response is compared against a stored value. Corrosion or fouling of the process elements is identified based upon the comparison between the measured frequency response and the stored value.

30 Claims, 6 Drawing Sheets

U.S. PATENT DOCUMENTS

| | | | |
|---|---|---|---|
| 5,526,689 A * | 6/1996 | Coulter et al. | 73/592 |
| 5,571,944 A * | 11/1996 | Pfeifer et al. | 73/24.04 |
| 5,594,180 A * | 1/1997 | Carpenter et al. | 73/861.356 |
| 5,646,338 A | 7/1997 | Mercusot et al. | 73/86 |
| 5,691,896 A | 11/1997 | Zou et al. | 364/157 |
| 5,734,098 A | 3/1998 | Kraus et al. | 73/61.62 |
| 5,741,978 A | 4/1998 | Gudmundsson | 73/861.04 |
| 5,861,560 A | 1/1999 | Harvey | 73/861.18 |
| 5,926,096 A | 7/1999 | Mattar et al. | 340/606 |
| 6,123,144 A | 9/2000 | Morman et al. | 165/104.32 |
| 6,186,004 B1 * | 2/2001 | Kaduchak et al. | 73/596 |
| 6,290,778 B1 | 9/2001 | Zugibe | 134/1 |
| 6,367,328 B1 * | 4/2002 | Gorman et al. | 73/592 |
| 6,471,823 B1 | 10/2002 | Stewart | 159/47.1 |
| 6,490,927 B2 * | 12/2002 | Braunling et al. | 73/597 |
| 6,594,603 B1 | 7/2003 | Eryurek et al. | 702/104 |
| 6,595,059 B2 * | 7/2003 | Gorman et al. | 73/592 |
| 6,601,005 B1 | 7/2003 | Eryurek et al. | 702/104 |
| 6,606,573 B2 * | 8/2003 | Wheeler | 702/56 |
| 6,675,655 B2 * | 1/2004 | Broden et al. | 73/716 |
| 6,717,658 B1 | 4/2004 | Saini et al. | 356/70 |
| 6,782,762 B2 * | 8/2004 | Cage | 73/861.355 |
| 6,823,736 B1 * | 11/2004 | Brock et al. | 73/587 |
| 6,871,148 B2 * | 3/2005 | Morgen et al. | 702/48 |
| 6,891,477 B2 * | 5/2005 | Aronstam | 340/606 |
| 6,912,918 B1 * | 7/2005 | Lynnworth et al. | 73/861.26 |
| 6,915,242 B2 * | 7/2005 | Ghaoud et al. | 702/189 |
| 7,043,969 B2 * | 5/2006 | Matsiev et al. | 73/54.41 |
| 7,148,611 B1 * | 12/2006 | Liu | 310/366 |
| 2001/0033631 A1 | 10/2001 | Sakamaki | 376/305 |
| 2002/0029572 A1 | 3/2002 | Kangai et al. | 60/685 |
| 2002/0078752 A1 | 6/2002 | Braunling et al. | 73/627 |
| 2003/0041653 A1 | 3/2003 | Matsiev et al. | 73/54.25 |
| 2003/0042007 A1 | 3/2003 | Sandu et al. | 165/94 |
| 2003/0056607 A1 | 3/2003 | Aronstam | 73/865.8 |
| 2003/0118150 A1 | 6/2003 | Hirabayashi et al. | 378/59 |
| 2003/0121338 A1 * | 7/2003 | Yates | 73/865.8 |
| 2003/0183537 A1 | 10/2003 | Eden et al. | 205/775.5 |
| 2005/0011278 A1 * | 1/2005 | Brown et al. | 73/861.18 |
| 2005/0145019 A1 * | 7/2005 | Matsiev et al. | 73/53.01 |

FOREIGN PATENT DOCUMENTS

| | | |
|---|---|---|
| CN | 1188546 A | 7/1998 |
| CN | 1269051 A | 10/2000 |
| DE | 3913715 A1 | 11/1989 |
| GB | 2 064 124 A | 6/1981 |
| JP | 2003315254 A * | 11/2007 |
| SU | 1415169 A1 | 8/1988 |
| SU | 1509583 A1 | 9/1989 |

OTHER PUBLICATIONS

G. Asti et al. "The Activated Torsion Oscillation Magnetometer," Parma Italy, pp. 1-6.

Schmidt, Stepfan and Grimes, Craig A. "Elastic Modulus Measurement of Thin Films Coated onto Magnetelastic Ribbons," IEEE Transactions on Magnetics, vol. 37, No. 4, Jul. 2001, pp. 2731-2733.

Notification of Transmittal of the International Search Report and the Written Opinion—PCT/US2005/028980.

"Experience with the Acoustic Ranger—A Sound Method for Tube Inspection", by E.S. Morgan, *Materials Evaluation*, Sep. 1981, pp. 926-930.

Office Action from the correspondence Chinese patent application Serial No. 200480026930.9, dated Apr. 11, 2008.

Office Action from the correspondence Russian patent application Serial No. 2007110645/28(011574), dated Mar. 22, 2007; 8 pages.

Decision on Grant from the corresponding Russian patent application Serial No. 2007110645, dated Feb. 27, 2009.

Communication pursuant to Article 94(3) EPC for related Application No. 05812711.9-1240 dated Jan. 13, 2010; 3 pages.

"Communication Pursuant to Article 94(3) EPC" for related Application No. 05812711.9-1240 date Jul. 22, 2009; 4 pages.

Office Action from the correspondence Russian patent application Serial No. 2007110645/28(011574), dated Nov. 20, 2008; 12 pages.

Office Action dated Aug. 12, 2010 for counterpart Chinese Patent Application No. 200580028304.8, filed Aug. 2, 2005.

* cited by examiner

FOULING AND CORROSION DETECTOR FOR PROCESS CONTROL INDUSTRIES

The present application is a Continuation-In-Part of and claims priority of U.S. patent application Ser. No. 10/893,144, filed Jul. 16, 2004 now U.S. Pat. No. 7,290,450.

BACKGROUND OF THE INVENTION

The present invention generally relates to a fouling and corrosion detector for industrial processes, and more particularly, to a field-mounted detector for predicting fouling and corrosion of process elements in an industrial process.

Generally, the term "fouling" refers to a build up of surface agents on a surface. Fouling is a common source of failure in heat exchangers, and can be difficult to detect. Heat exchangers are devices that facilitate, for example, the transfer of heat between a process and a fluid circulating within the exchanger. Heat exchangers are used in a number of industrial systems, including reactors, boilers and the like.

Facilitating this thermal exchange is an exchanger core comprised of one or more tubes through which a fluid is continually circulated. As used herein, the term "fluid" refers to a process material in liquid or gaseous state. The fluid is circulated through the exchanger core. In some embodiments, the fluid may be steam, or high or low temperature process materials, which may have corrosive properties.

Generally, the exchanger core is positioned adjacent to and/or in contact with vessels, conduits, or other components of the industrial process so that heat can be transferred between the process and the circulating fluid within the exchanger. Typically, the fluid within the heat exchanger is fed into the exchanger, circulated through the exchanger, and collected on the other side of the exchanger. In many instances, the collected fluid is recycled and re-circulated. Recycling refers to a process of heating or cooling the collected fluid according to the specific implementation. For example, if the fluid circulated through the exchanger is steam, then condensed steam is collected, reheated until its changes phase back to steam, and then circulated back through the exchanger.

Depending on the material used, the circulating fluid that passes through the exchanger may cause corrosion or may contain solids that can plug or coat the exchanger, thereby reducing the efficiency of the heat exchange process. In general, corrosion and fouling may cause significant problems in an exchanger in an industrial process. For example, if a heat exchanger becomes plugged due to fouling or if it fails due to corrosion (such as because seals become corroded and pressure is lost), process fluid fails to circulate through the exchanger core and the efficiency of the heat exchange may be compromised. Additionally, if the exchanger core is used to deliver heat to a process or to remove heat from a process and the exchanger becomes plugged, the process may not reach the desired temperature. Additionally, the process material that exchanges heat with the fluid in the exchanger core may foul or corrode the core from the outside, rendering the exchanger core inefficient.

When an exchanger core becomes fouled or corroded, typically the system is shut down so that the core can be serviced (unplugged, replaced or otherwise repaired). If an exchanger core fails during operation, not only is the system shut down, but the batch may need to be discarded. It is generally desirable to identify impending fouling and/or corrosion and to service the core before it fails.

In the process industry, unplanned plant downtime can be very expensive due both to loss of production and to the cost of shutdown/start up. Although it varies by industry, scheduled maintenance is often much less expensive than a complete plant shut down. The events that lead to unplanned plant downtime can also result in safety issues, environmental issues, and defective products.

Devices for producing diagnostic information and generating alarms are used in process control industries to avoid such unplanned events when possible. Generally, process variable are monitored, and if predetermined limits are exceeded, an alarm condition is reported. Usually the alarm is indicative of a process variable that is out of normal range. The cause is left to be determined or to be inferred from other information available, either in the control room or at the instrument generating the alarm. Conventionally, detection of plugging or coating required a sophisticated analysis of complex Pressure-Volume relationships to determine if the energy balance or efficiency had degraded from a known baseline condition.

SUMMARY

A method for inferring possible or impending corrosion or fouling of process elements from fluid flowing in a pipe of an industrial process is described. A frequency response of a body is measured. The measured frequency response is compared against a stored value. Corrosion or fouling of the process elements is identified based on the comparison. In one embodiment, characteristics of the types of corrosion or fouling are inferred based on the comparison.

DETAILED DESCRIPTION

Generally, the present invention relates to a device that can be inserted in a process flow, preferably upstream from process elements, and that can be used to predict downstream fouling and corrosion conditions based on a resonant frequency of the device. The present invention also relates to techniques for predicting fouling and corrosion (or plugging) of process components based on a frequency response of a device positioned upstream from the process components.

Figure 1:
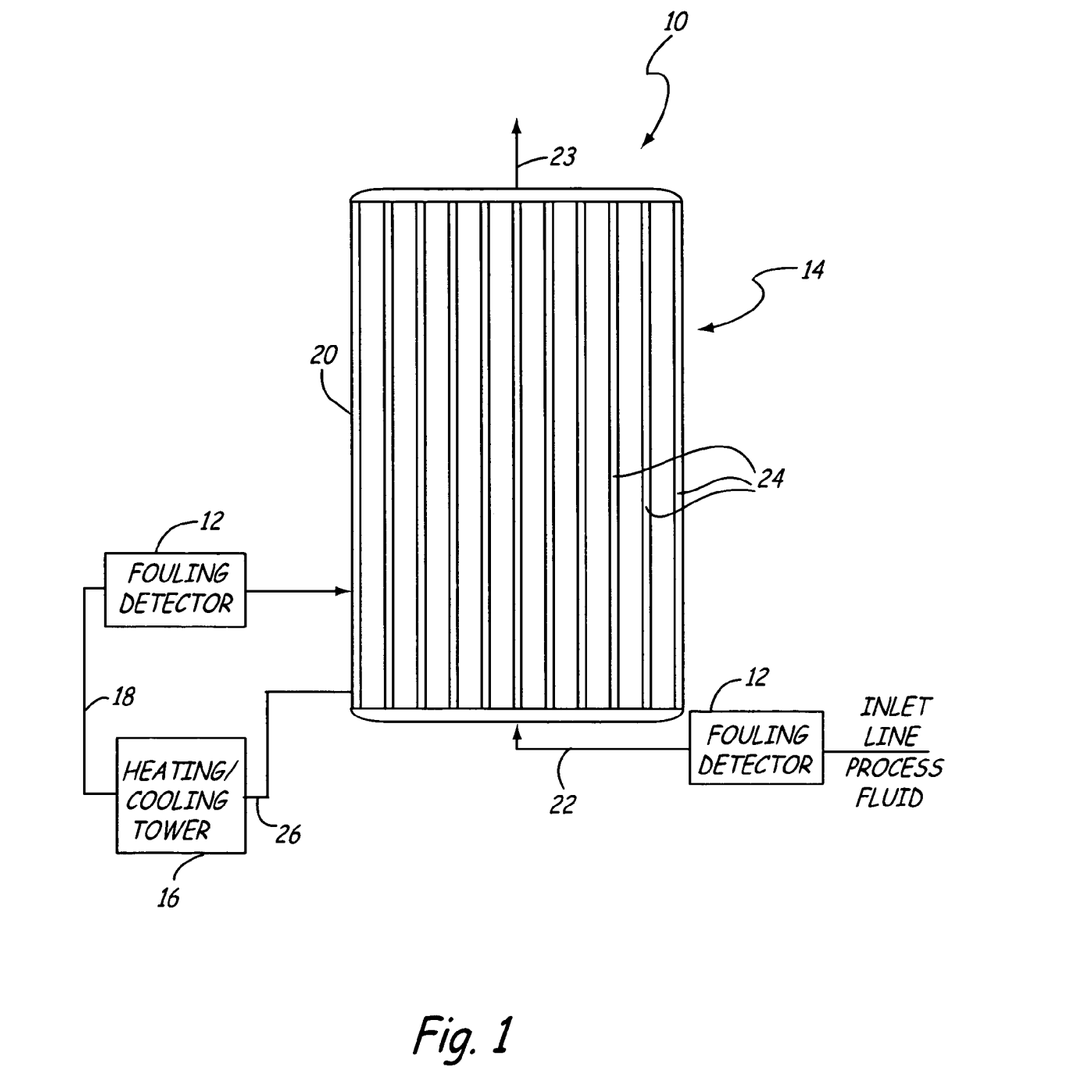
FIG. 1 is a simplified block diagram of a fouling and corrosion detector system according to an embodiment of the present invention.

FIG. 1 shows a simplified block diagram of a of an industrial process 10, including fouling detectors 12 and a heat exchanger 14. The heat exchange system includes a fouling detector 12 positioned upstream from a heat exchanger 14, which is in turn coupled to a recycling tower 16 according to an embodiment of the present invention. Many components of the heat exchange system, which are conventional in design and not part of the present invention, have been omitted or simplified, including many elements of the heat exchanger 14 and the recycling tower 16.

Generally, fluid is processed by the recycling tower 16, flows through pipe 18, past the fouling detector 12 and enters the shell 20 of the heat exchanger 14. The fluid exchanges heat energy with the process fluid, which in this embodiment is fed into the heat exchanger 14 via inlet line 22 and circulated through tubes 24 within the heat exchanger 14. Used fluid exits the heat exchanger 14 via line 26 and may be circulated through the recycling tower 16 and back into the exchanger 14. The process fluid, which entered vial inlet line 22 flows through the exchanger and flows out via outline line 23.

Generally, the recycling tower 16 may be a heating tower or a cooling tower. Alternatively, the recycling tower 16 may perform some other operation on the used fluid before recirculating the fluid through the exchanger 14.

The fluid flows around fouling detector 12 before flowing into the heat exchanger 14. By positioning the fouling detector 12 upstream of the heat exchanger 14, it is possible to predict corrosion or fouling of the exchanger core 14 by the process fluid, in part, based on a resonant frequency of the fouling detector 12.

A second fouling detector 12 is positioned upstream from the exchanger and coupled to the process fluid inlet line 22. The second fouling detector 12 is utilized to detect possible or impending fouling or corrosion of the inlet line 22 upstream from and within the exchanger core 14.

As described below, the fouling detector 12 is comprised of an obstructing body or element, which extends into the fluid flow. A sensor is coupled to the body to detect its resonant frequency. In some embodiments, the body is excited into resonance by the fluid flow. In other embodiments, the body may be excited into resonance using a piezoelectric element. In either instance, the resonant frequency of the obstructing body changes as the mass of the body changes due to fouling or corrosion, thereby predicting possible or impending fouling or corrosion of downsteam elements.

In the embodiment of FIG. 1, two fouling detectors 12 are provided, one for the process fluid and one for the heating/cooling fluid. However, any number of fouling detectors 12 may be utilized. In some systems, one fouling detector 12 may be sufficient to predict impending fouling or corrosion conditions.

Figure 2:
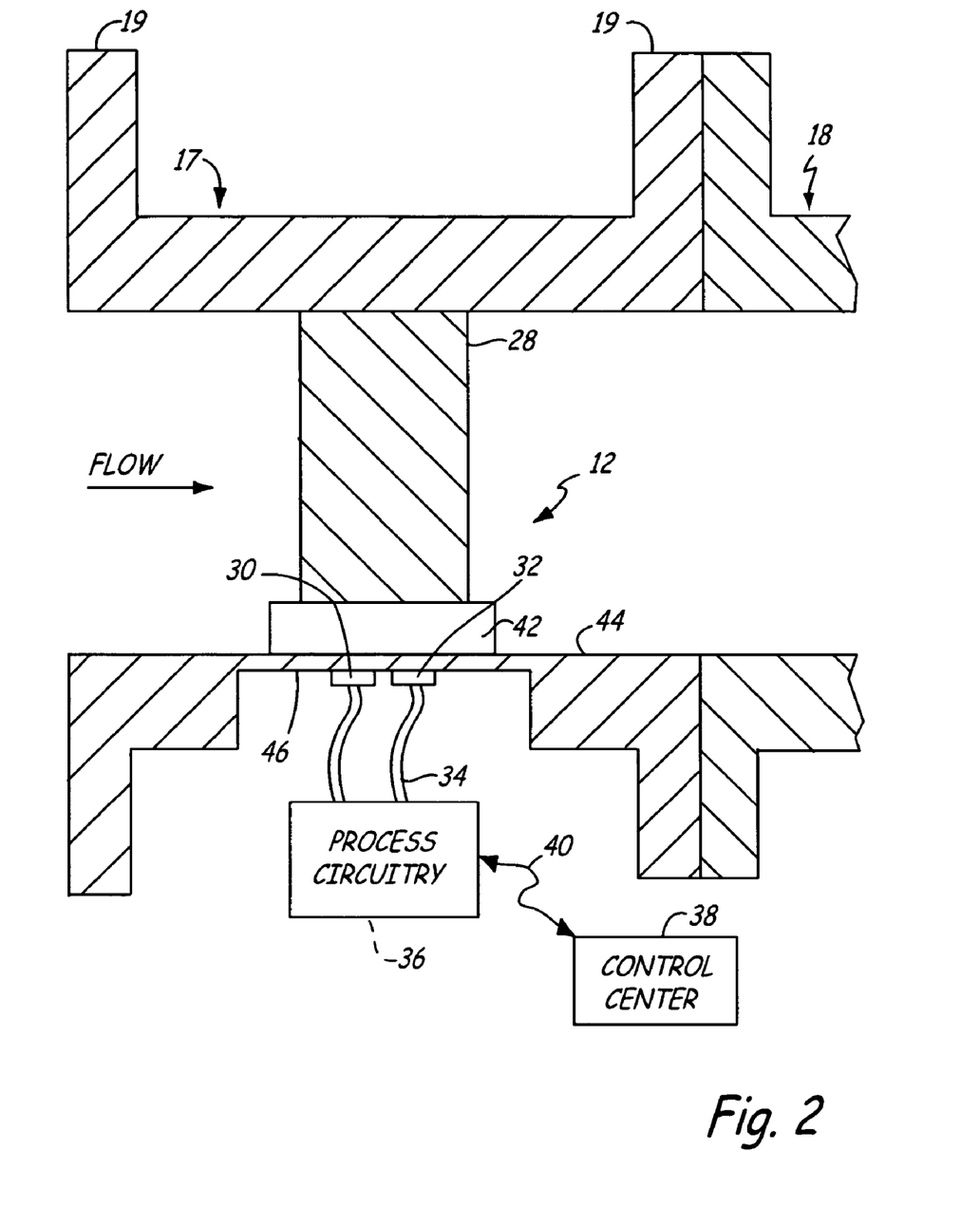
FIG. 2 is a cross-sectional view of a fouling and corrosion detector according to an embodiment of the present invention.

It is appreciated that though various embodiments have been described in the context of the diagnosing of fouling or corrosion in a heat exchanger, the present invention may be utilized in many different applications in which it is desirable to determine fouling or corrosion in a fluid flow of a process fluid. FIG. 2 illustrates a simplified cross-sectional view of a fouling detector 12 in situ according to an embodiment of the present invention. Fouling detector 12 includes resonating body or body 28 disposed in pipe segment 17, which is provided with flanges 19 for attachment to the process pipe 18. Generally, the body 28 is sized to obstruct (at least partially) fluid flow through the pipe 18. The body 28 is preferably coupled to a piezoelectric element 30 and to a sensor 32, both of which may be connected by leads 34 to process circuitry 36. Process circuitry 36 may include a transceiver adapted to communicate with a control center 38 via communications link 40. Process circuitry 36 may also include a driving circuit for driving the piezoelectric element 30 in order to shake the body 28.

The body 28 is attached to a base 42, which is coupled to the wall 44 of pipe segment 17 in a region of reduced thickness (sometimes referred to as a flexure 46). The region of reduced thickness 46 produces a measurable strain in response to movement of the body 28.

An initial resonant frequency of the fouling detector is a function of flexure stiffness, mass of the body 28, and to a lesser extent damping. As process material fouls or corrodes the surface of the detector 12, the resonant frequency changes. This change in resonant frequency is based on a change in the mass of the body 28, and can be correlated to the amount, or thickness of fouling present (based on mass increase) or to the amount of corrosion or erosion (based on a mass loss) of the detector 12. When the mass change is significant enough, an alarm or alarm condition can be triggered and an alarm signal can be generated and communicated to the control center.

Generally, the alarm provides notice that the downstream components of the process may be corroded or fouled. This allows the plant maintenance staff to take appropriate preemptive action to prevent an unplanned plant shutdown. Thus, the fouling/corrosion detector provides a quantitative measure from which possible or impending fouling or corrosion of process elements may be inferred.

As previously discussed, the piezoelectric element 30 is coupled to the body 28. A frequency sweep of the piezoelectric element 30 "shakes" the body 28 (causing the body 28 to oscillate). The sensor 32 monitors the oscillations of the body 28 to detect a resonant frequency of the body 28.

In general, resonant frequency is one parameter that can be utilized to detect fouling and/or corrosion of the body 28, and therefore, by implication, fouling and/or corrosion of the exchanger. Specifically, both fouling and corrosion alter the mass of the body 28 (by increasing the mass of the body in the case of fouling, and by decreasing the mass of the body in the case of corrosion). The resonant frequency is partially dependent on the mass, and a change in mass (however slight) is detectable as a shift in the resonant frequency.

During installation, the piezoelectric element 30 is excited in order to shake the body 28. The sensor 32 measures a baseline resonant frequency, which can be stored in a memory of the process electronics 36. Periodically, during operation or between batches, the body 28 is again shaken, and the resonant frequency is measured. The measured resonant frequency is then compared against the baseline resonant frequency. If the measured resonant frequency of the obstruction varies outside of a predetermined range relative to the baseline, an alarm may be generated, indicating that the exchanger should be cleaned, inspected or otherwise serviced prior to further processing.

Another parameter that can be utilized to detect fouling or corrosion is the power necessary to drive the piezoelectric element 30. The resonant frequency of the body 28 corresponds to a power "sweet spot" or local power minimum. In particular, the power necessary to drive the system is typically at a minimum at the resonant frequency. If a piezoelectric element 30 is utilized to drive the system, the piezoelectric element 30 can also be utilized as a coarse amplitude-measurement device, to measure the amplitude of the oscillations.

The fouling and corrosion detector is designed to detect the resonant frequency of the obstruction with a frequency sweep, which can, in a preferred embodiment, be centered around the likely resonant frequency. It is possible that given a favorably designed resonant point that the process noise by itself could excite the structure into resonance. In that case, only an accelerometer is required to measure frequency and amplitude of the oscillations.

In general, any change in mass associated with the obstruction results in a change in the frequency response. For example, if the body becomes coated or fouled, the body 28 would generally display a lower resonant frequency than the baseline. A magnitude of the shift in resonant frequency would be dependent upon the nature and amount of the build up. For example, a sticky or gooey build up might increase the damping coefficient and lower the Q factor. Increased damping of the resonant frequency without adding mass, would change the apparent resonant frequency with respect the natural resonant frequency. While this might not be as big an effect as the change in mass, it is still readily detectable.

If the device were used to detect corrosion or erosion of the obstruction, then the erosion of material from the obstruction would increase the resonant frequency relative to the natural resonance. The magnitude of the shift in resonant frequency would be dependent on the amount of mass lost to the erosion process. A decrease in damping alone, without adding mass, would also change the apparent resonant frequency with respect to the natural resonant frequency.

It will be understood by a worker skilled in the art, upon reading this disclosure, that the system of the present invention can generally be modeled as a second order system (or at least may look like a system of second order) that is underdamped. In general, the resonant frequency and damping coefficient are better measures of an underdamped second order system.

An alternative strategy for detecting a mass change of the body 28 is to measure any change in the frequency response including the Q factor, the phase margin, the gain margin and the like. In general, any change in the frequency response of the system to the frequency sweep (as compared to the baseline) would indicate a corrosion or erosion or mass gain event. Any change may be an indication that the exchanger is becoming plugged or corroded. The effect of the various changes in resonant frequency would vary depending on the nature of the build up or corrosion. If the build up material is massive, but granular (low viscosity), the Q factor and the phase shift would not change much, but the resonant frequency would change, with only a minimal change in damping. However, if the build up material is highly viscous, then both the Q and the phase margin would change as well as the resonant frequency.

A powerful advantage of the present invention over prior art detectors is that the resonant frequency of the body 28 can be monitored to determine, not only whether corrosion or fouling is occurring, but also what type of build up is occurring (viscous or granular).

Fouling and corrosion detector 12 may have the additional advantage that if the body 28 is positioned at the bottom of the pipe 18, solids that are not dissolved within the fluid flow may catch on the body 28 instead of flowing into the exchanger and plugging the system. Such solids may be detected by noting a change in the frequency response of the body 28 due to a change in mass or by detecting a sudden, unexpected movement of the body. Thus, the detector 12 provides an early warning system (a predictive measure) of the condition of downstream process elements, such as a heat exchanger, a venturi pipe, an annubar, and the like.

In general, the body 28 may be formed in a variety of different shapes, each of which may provide resonant characteristics that are optimized for a particular application.

For example, in one embodiment, the body may be formed with a flat surface facing into the fluid flow and with recessed areas disposed behind the flat surface, thereby creating vortices and isolating small fluid pockets from the fluid flow. This may, in some instances, facilitate corrosion of the body in areas that are shielded from the direct force of the fluid flow. In another embodiment, the body is formed of different materials along its surface, each material being reactive with a different ion or molecule within the fluid flow, such that the presence of any of the reactive ions or molecules will cause a mass change in the body. The different materials can be selected according to materials used to form downstream elements.

Additionally, a neural network, artificial intelligence agent, or other analysis tool may be utilized to infer fouling and corrosion conditions from measured resonant frequency values. While these elements are not shown, it should understood that the detection of fouling or corrosion and the generation of an associated alarm signal may be automated using such systems for the analysis of process data derived from the fouling/corrosion detector.

Figure 3:
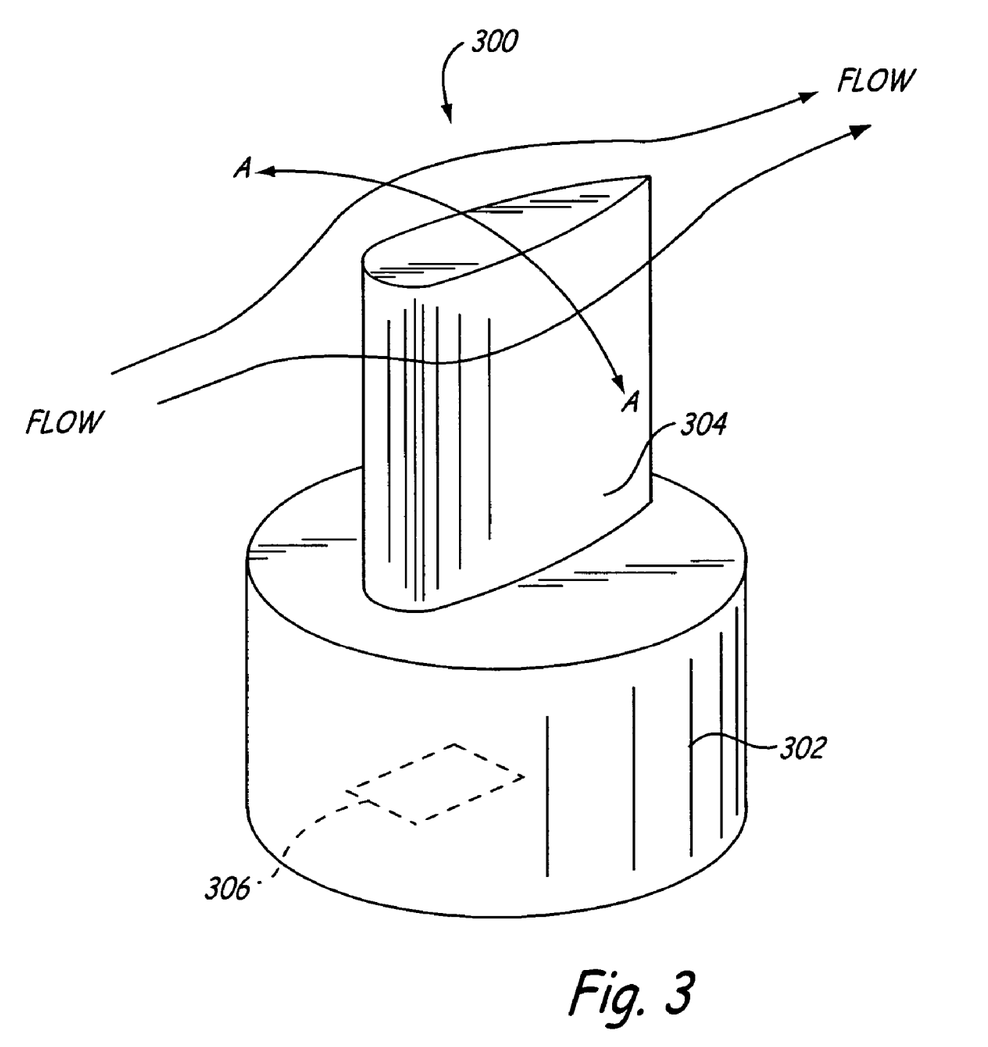
FIG. 3 is a perspective view of a resonating body according to an embodiment of the present invention.

FIG. 3 illustrates a top plan view of a resonating body 300 according to an embodiment of the present invention. The resonating body 300 has a body 304 coupled to a base 302, which is in turn coupled to a wall of the pipe (not shown). In this embodiment, the resonating body 300 is shown having tear-drop type shape so as to minimize the obstruction to the fluid flow while providing a surface for corrosion and/or fouling.

In a preferred embodiment, the bluff body is a wing-shaped body, and excited by a piezoelectric transducer 306 in the base. The flexure (not shown) is developed as a thin disc structure that is integral to the base and on which the wing-shaped bluff body is mounted. Electronics (not shown) to drive the piezoelectric transducer, to sense the change in resonant frequency, and to communicate an alarm condition are externally mounted from the process. Such electronics can be either close coupled or remotely mounted.

This type of fouling detector can also output a signal that is proportional to coating build up. For some process fluids, estimated process fluid visosity changes over time would be required to make this build measurement more accurate.

Figure 4:
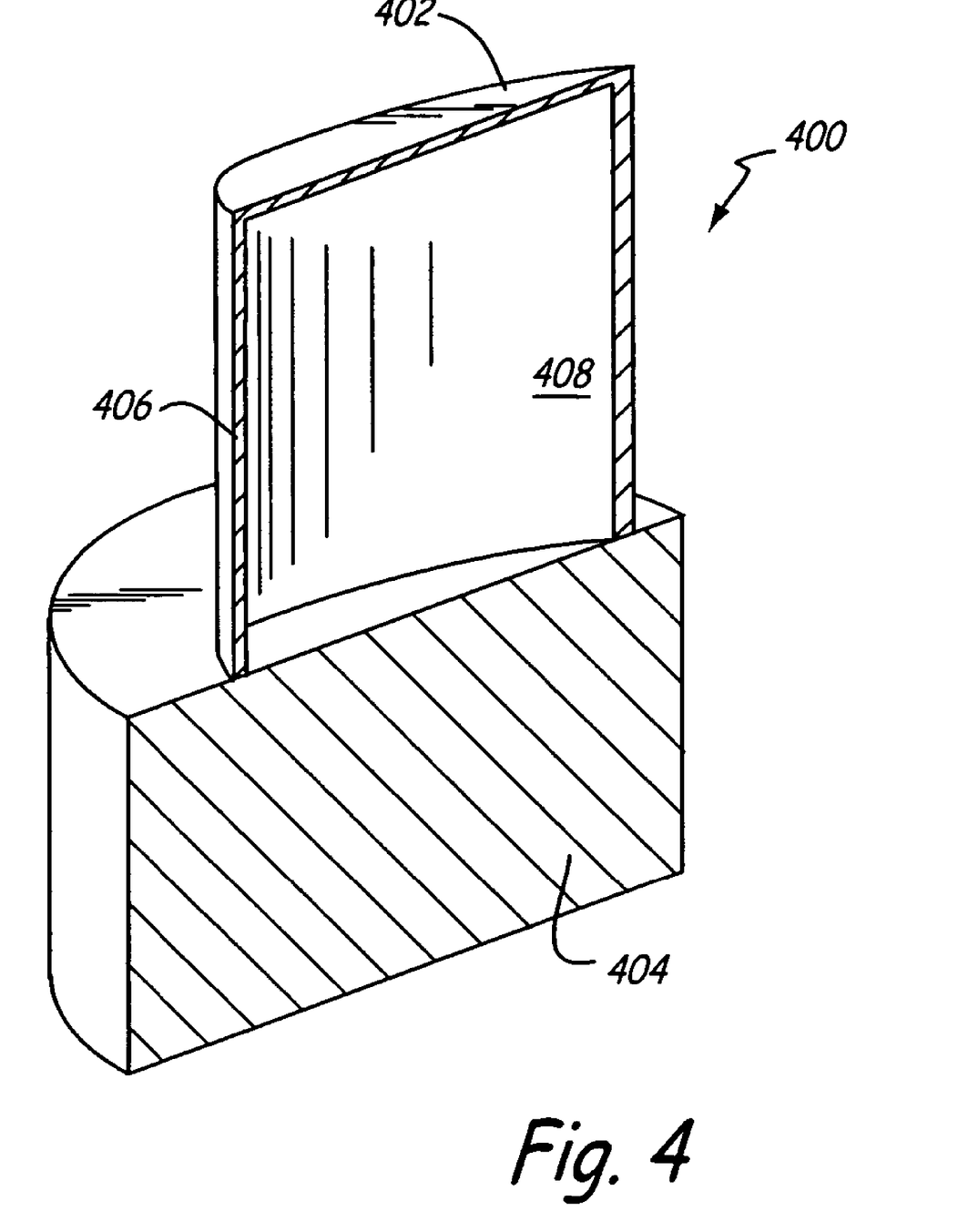
FIG. 4 is a perspective view of a thin-shell resonating body according to an embodiment of the present invention.

FIG. 4 illustrates an alternative embodiment of the resonating body 400 shown in cross-section. Resonating body 400 has a body 402 coupled to a base 404, which in turn is coupled to a wall of a pipe (not shown). In this embodiment, the body 402 has a thin wall 406 defining a hollow chamber 408. The resonant frequency of the resonating body 400 may be determined to provide a baseline resonant frequency, which can be stored in a memory of the device electronics. When the corrosive fluid flow corrodes entirely through the thin wall 406, the chamber 408 fills with fluid and the resonant frequency of the resonating body 400 changes dramatically. Alternatively, the fluid filling the chamber 408 is likely to cause movement of the body 402 that is different from the normal motion during operation.

While the gradual corrosion of the thin wall 406 can also be detected using the frequency response as described above, the predetermined alarm condition may be set fairly high, so that small variations can be monitored without triggering an alarm condition. When the fluid fills the chamber 408, the frequency response varies dramatically as the process fluid radically changes the mass of the resonating body 400, thereby triggering an alarm.

The thin wall 406 of the body 402 may be formed from a material selected so as to react with the fluid flow. In general, the material selected for thin wall 406 is designed to react with the process fluid at a rate corresponding to or slightly faster than the estimated rate of corrosion or coating by other elements of the system. Additionally, the wall thickness itself may be designed to correlate to a rate of corrosion or erosion, such that when the process fluid breaches the wall, the alarm signal is generated.

Figure 5:
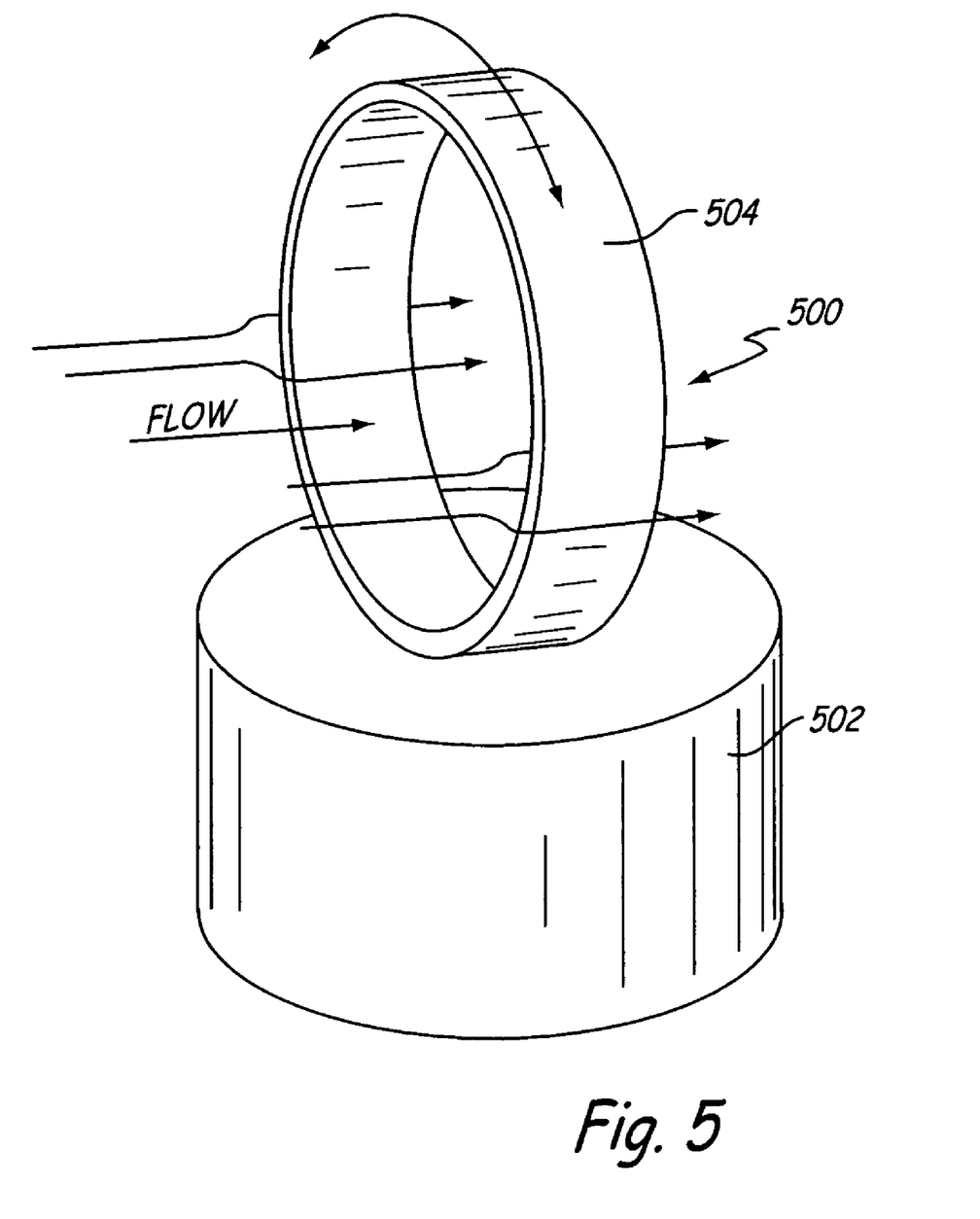
FIG. 5 is a perspective view of a ring-shaped resonating body according to an embodiment of the present invention.

FIG. 5 illustrates a plan view of a resonating body 500 according to an embodiment of the present invention. The resonating body 500 has a ring-shaped body 504 coupled to a base 502, which is in turn coupled to a wall of the pipe (not shown). In this embodiment, the body 504 is oriented perpendicular to the direction of flow of the fluid so as to minimize the obstruction to the fluid flow while providing a surface for corrosion and/or fouling. Geometry for the ring-shaped body 504 can be specified to correspond to the geometry of the tubing used in the exchanger in order to correlate the fouling of the ring-shaped body 504 to the geometry to the exchanger itself.

In each embodiment shown in the figures and described above, the detector includes a body that serves as a partial obstruction to the fluid flow. The body may be conceptualized as a "sacrificial lamb" for early detection of coating or corrosion. In one embodiment, the surface of the body facing into the fluid flow may vary according to the fluid properties in order to facilitate fouling or corrosion of the body. For example, for certain types of fluid, it may be desirable to provide a fluid facing surface that is relatively flat to facilitate coating. Other shapes that promote coating and/or corrosion may be devised and implemented. For example, as previously discussed, the surface facing into the process flow may provide a sacrificial surface for reacting with a corrosive process fluid, such that the fluid pits or erodes the surface.

Regardless of the specific shape of the detector, the control center may periodically initiate a frequency sweep of a fouling detector, exciting the piezoelectric element and thereby causing the body of the detector to oscillate. The sensor, either disposed on the body or at its base, can be used to detect the resonant frequency of the body.

A change in mass of the body, either mass loss or mass gain, can be detected by comparing a measured resonant frequency against a stored resonant frequency (a baseline frequency). If the change falls outside of a predetermined range, an alarm may be initiated.

In general, it is desirable that the supporting materials, both for the body and for other materials of the system resist corrosion or erosion from the application process fluid or gas. However, as corrosion/erosion process removes material from the body, the resonant frequency increases. At a predetermined amount of material lost, the device sends an alarm signal or caution that a potential corrosion problem exists.

In general, there are a number of advantages to the fouling and corrosion detector of the present invention. First, the fouling and corrosion detector provides a sensitive, predictive method determining the extent of exchanger fouling. The body provides a simple application and mounting, does not require multiple pressure and volume analyses to provide information on fouling or corrosion. Maintenance is straightforward, because the detector is serviced when the exchanger is services, either by cleaning or replacing the body. Additionally, the fouling and corrosion detector of the present invention provides a direct in-process corrosion/erosion sensing mechanism without electrodes or electronic contacts. Corrosion/erosion sensing can be configured to provide an alarm signal with ample factors of safety.

Sensitivity of the detector can be increased by using the thin skin/hollow core body technique for critical corrosion monitoring applications. For most applications, 4-20 milliAmp loop power would be more than sufficient to power the detector. However, it may also be possible to steal power from a 4-20 milliAmp loop by storing it capacitively for small bursts of activity. In general, the present invention lends itself to such an arrangement, because fouling and corrosion take place over time and constant monitoring is not required.

Figure 6:
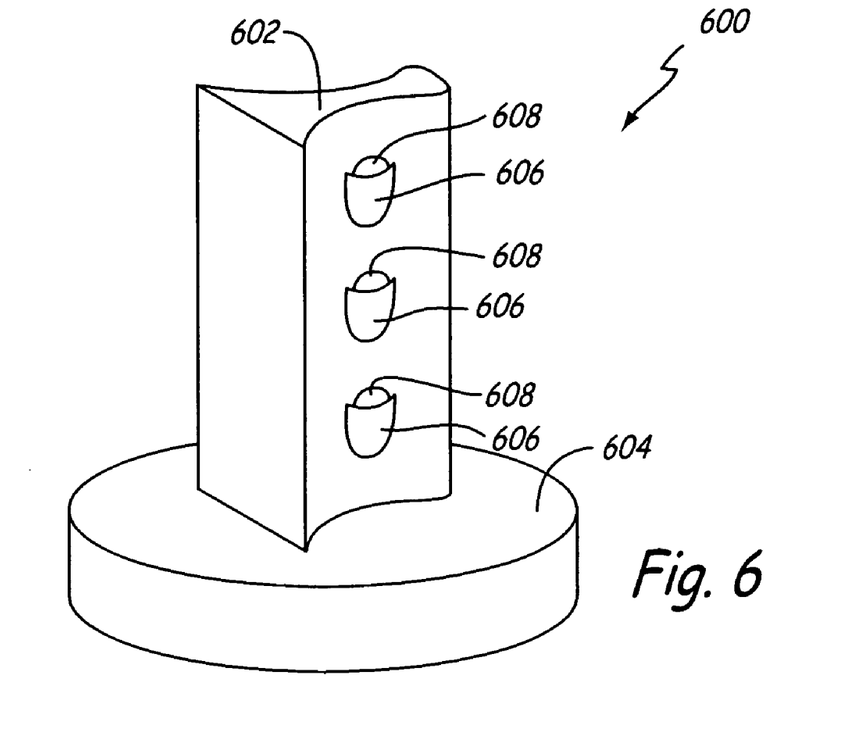
FIG. 6 is a perspective view of a resonating body with pockets for securing corrodible inserts according to an embodiment of the present invention.

FIG. 6 illustrates a resonating body 600 having a body 602 mounted to a base 604. The body 602 having one or more pockets 606 (or alternatively recesses) sized to receive and retain corrodible inserts 608. In one embodiment, the body 602 and pockets 604 are formed from stainless steel. The corrodible inserts can be selected according to corrosion or fouling properties consistent with materials in downstream process elements, such that corrosion or fouling of the inserts is indicative of possible corrosion or fouling of downstream elements. In order to maintain the resonant frequency, the pockets 604 would preferably be arranged symmetrically about the body 602.

It will be understood by workers skilled in the art that the body may preferably be formed in or welded into a pipe section, which can be attached into a process by welding, or preferably via flange elements. The corrodible inserts 608 can be inserted into the body 602 prior to positioning the pipe section into the process. In this embodiment, upon detection of possible corrosion and during the servicing of the downstream elements, the pipe section is removed, the corrodible inserts 608 are replaced, and the pipe section is reinserted into the process.

Figure 7:
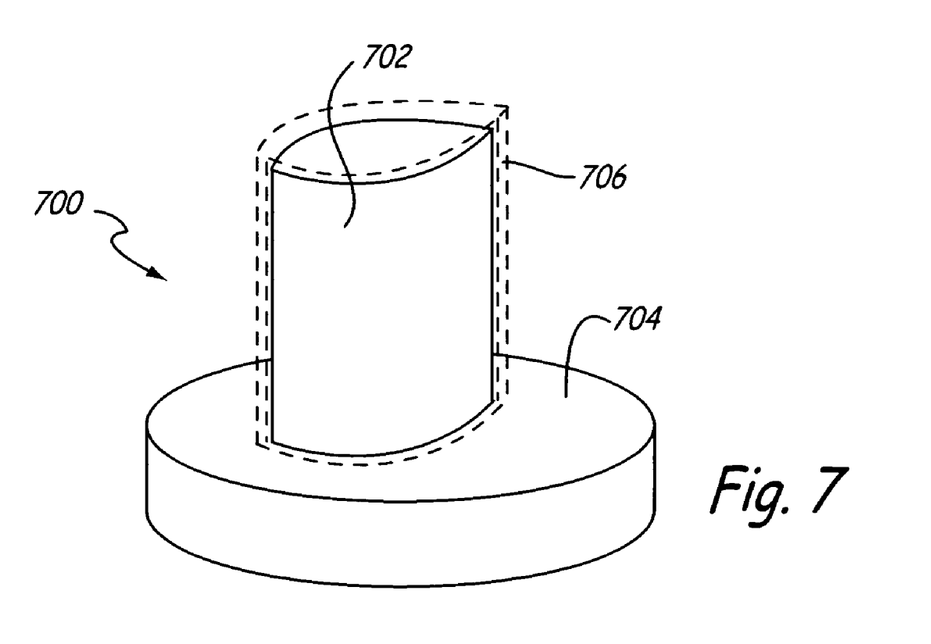
FIG. 7 is a perspective view of a resonating body with a corrodible cover according to an embodiment of the present invention.

FIG. 7 illustrates a resonating body 700 having a body 702 mounted to a base 704, wherein a cover layer 706 (shown in phantom) is disposed over the body 702. The cover layer 706 may be a slip cover or may be a deposited cover layer, which preferably is formed from a corrodible material. The corrodible cover 706 provides a replaceable element, allowing the resonating body to be reused multiple times simply by replacing the corrodible cover 706 with a new cover as needed. Additionally, a corrodible cover 706 makes the resonating body 700 scalable to the process. For example, in some processes, it may be that downstream elements require servicing after three corrodible covers have been used up. In such an instance, it is possible to layer multiple corrodible covers 706 over the body 702. In this case, a change in mass corresponding to corrosion through all of the corrodible layers causes the resonating body 700 to generate an alarm condition indicative of potential corrosion downstream. The resonating body 700 is then removed, the covers 706 are replaced, and the resonating body 700 is reinstalled.

As previously mentioned, the present invention is intended for use as a predictor of potential downstream fouling and/or corrosion. In one embodiment, each time the frequency response of the detector changes outside a predetermined range, the alarm is triggered and the detector body is replaced. In an alternative embodiment, the detector body is simply recalibrated for a new baseline and the alarm is reset for a change in the frequency response relative to the new baseline. In a third embodiment, the body is corrosion resistant and is provided with one or more replaceable and corrodible elements (inserts or covers) for reacting with the fluid.

While the present invention was introduced with respect to heat exchangers, the fouling and corrosion detectors of the present invention may be employed in any fluid flow. Additionally, though FIG. 2 illustrated the body extending a full diameter of the pipe segment, the body need only extend into the flow. Finally, it should be understood that slight changes in mass caused by fouling or corrosion are readily detectable based on the frequency response of the body, and an inference of possible corrosion or fouling may include analysis of frequency response to identify characteristics of the corrosion or fouling, based on the resonant frequency response of the obstruction. For example, changes in the Q factor or damping coefficients of the frequency response may indicate whether the fouling is granular or sticky. Moreover, a, shift in the resonant frequency (higher or lower) can be used to distinguish between fouling and corrosion based on increase or decrease in the mass of the obstruction. A decrease in the resonant frequency is generally indicative of a fouling condition characterized by increased mass of the obstruction. An increase in the resonant frequency is generally indicative of a corroded condition characterized by a decrease in mass of the obstruction. Other characteristics of the frequency response, including peak resonant frequency, damping coefficients, and the like may be correlated to other impending fouling or corrosion conditions.

Although the present invention has been described with reference to preferred embodiments, workers skilled in the art will recognize that changes may be made in form and detail without departing from the spirit and scope of the invention.

What is claimed is:

1. A method for inferring possible corrosion of process elements from process fluid flowing in a pipe of an industrial process, the method comprising:
    mounting a body in the pipe which is exposed to the flow of process fluid to which a process element is exposed, the body comprising a structure extending into the pipe;
    measuring a frequency response of the body disposed in the pipe with a sensor coupled to the body;
    comparing the measured frequency response to a stored value; and
    inferring corrosion of the process element based upon the comparing.

2. The method of claim 1 wherein before the step of measuring, the method further comprises:
    installing the body in the pipe, the body at least partially obstructing the fluid flow;
    measuring a frequency response of the body; and
    storing a value based on the measured frequency response.

3. The method of claim 2 wherein the step of measuring further comprises:
    performing a frequency sweep of a piezoelectric element coupled to the body; and
    measuring a resonant frequency of the body.

4. The method of claim 1 further comprising:
    identifying a resonant frequency of the frequency response;
    wherein an increase in the resonant frequency is indicative of corrosion.

5. The method of claim 4 wherein a magnitude of the increase is indicative of an extent of corrosion.

6. The method of claim 1 and further comprising:
    generating an alarm if the change is outside a predetermined range, the alarm being indicative of corrosion of the process element downstream of the resonating body in the pipe.

7. The method of claim 1 wherein the structure comprises:
    one or more pockets disposed on the structure and adapted to secure one or more corrodible inserts; and
    wherein corrosion of the one or more corrodible inserts causes a change in the frequency response of the structure.

8. The method of claim 7 wherein each corrodible insert is selected according to its corrosion characteristics.

9. The method of claim 8 wherein the corrosion characteristics are selected to correspond to corrosion characteristics of the process elements in the pipe.

10. A device for inferring possible corrosion of process elements from process fluid flowing in a pipe of an industrial process, the device comprising:
    a body mounted in the pipe, the body comprising a structure extending into the pipe which is exposed to a flow of the process fluid to which a process element is exposed and adapted to move in response to an excitation; and
    a sensor coupled to the body and adapted to infer possible corrosion of the process element based on a change in a frequency response of the body.

11. The device of claim 10 wherein the body comprises:
    a hollow structure having a thin wall, the thin wall formed from a material selected to react with the fluid flow at a rate consistent with materials of the process elements.

12. The device of claim 10 wherein the structure comprises:
    a plurality of pockets disposed about the structure.

13. The device of claim 12 further comprising:
    a plurality of corrodible inserts, each corrodible insert sized to fit within one of the plurality of pockets.

14. The device of claim 13 wherein the corrodible inserts are formed from material selected to react with the fluid.

15. The device of claim 10 further comprising:
    a transmitter circuit adapted to generate an alarm signal if a change in the frequency response is outside of a predetermined range, the transmitter circuit for transmitting the alarm signal to a control center.

16. The device of claim 10 wherein the excitation comprises process noise sufficient to excite the body into resonance.

17. The device of claim 10 wherein the excitation comprises an excitation signal generated by a piezoelectric driver.

18. The device of claim 10 further comprising:
    a corrodible cover adapted to fit over the body, the corrodible cover formed from a material selected to react with the fluid.

19. The device of claim 10 wherein an increase in a resonant frequency of the body is indicative of corrosion of the body.

20. A method for inferring possible corrosion of process elements of an industrial process, the method comprising:
    mounting a body to the pipe, the body comprising a structure exposed to a process fluid to which a process element is exposed;
    shaking the body into resonance;
    detecting a change in a frequency response of the body relative to a stored value; and
    inferring corrosion of the process element based upon the detected change.

21. The method of claim 20 and further comprising:
    generating an alarm signal indicative of corrosion if the change is outside of a predetermined range.

22. The method of claim 20 wherein the step of shaking comprises:
    exciting a piezoelectric element coupled to the body with a frequency sweep, the frequency sweep exciting the piezoelectric element which in turn excites the body into resonance.

23. The method of claim 20 wherein the step of detecting comprises:
    measuring a frequency response of the body; and
    identify an increase in the frequency response as indicative of corrosion.

24. The method of claim 23 wherein the step of measuring comprises:
    detecting a local power minimum during a frequency sweep of a piezoelectric driving element that is coupled to the body.

25. The method of claim 20 wherein the body comprises:
    a hollow structure having a thin wall, the thin wall formed from a material selected to react with the fluid flow at a rate consistent with materials of the process elements.

26. The method of claim 20 wherein the structure comprises:

one or more pockets disposed on the structure.

27. The method of claim 26 wherein before the step of shaking, the method comprising positioning one or more corrodible inserts into the one or more pockets.

28. The method of claim 27 wherein the one or more corrodible inserts are formed from a material selected to react with the process fluid at a rate that is substantially similar to a rate of reaction of the process elements.

29. A method for inferring fouling process elements from fluid flowing in a pipe of an industrial process, the method comprising:

measuring a frequency response of a body disposed in the pipe;

comparing the measured frequency response against a stored value;

identifying fouling of the process elements based upon the comparing;

wherein the change in the frequency response is indicative of characteristics of a type of fouling; and wherein a decrease in a Q-factor and an increase in a damping coefficient of the frequency response is indicative of a build-up of a sticky material.

30. A device for inferring possible fouling of process elements from fluid flowing in a pipe of an industrial process, the device comprising:

a body disposed in the pipe and adapted to move in response to an excitation;

a sensor coupled to the pipe and adapted to infer possible fouling based on a change in a frequency response of the body;

wherein the frequency response is indicative of characteristics of a type of fouling; and wherein a decrease in a Q-factor and an increase in a damping coefficient of the frequency response is indicative of a build-up of sticky material on the body.

* * * * *